United States Patent [19]

Wolfe et al.

[11] Patent Number: 4,533,348
[45] Date of Patent: * Aug. 6, 1985

[54] IN-LINE DRUG DISPENSER FOR USE IN INTRAVENOUS THERAPY

[75] Inventors: Allan M. Wolfe, South Laguna; James M. Davenport, Tustin; Felix Theeuwes, Los Altos; Su I. Yum, Sunnyvale, all of Calif.

[73] Assignee: ALZA Corporation, Palo Alto, Calif.

[*] Notice: The portion of the term of this patent subsequent to Oct. 2, 2001 has been disclaimed.

[21] Appl. No.: 649,778

[22] Filed: Sep. 12, 1984

Related U.S. Application Data

[63] Continuation of Ser. No. 518,490, Jul. 29, 1983, Pat. No. 4,474,574, which is a continuation of Ser. No. 338,206, Jan. 11, 1982, abandoned.

[51] Int. Cl.$^3$ ............................................... A61M 5/14
[52] U.S. Cl. ........................................ 604/85; 604/92; 604/246; 137/268
[58] Field of Search ...................... 604/85, 83, 84, 56, 604/92, 246; 137/268

[56] References Cited

U.S. PATENT DOCUMENTS

| | | | |
|---|---|---|---|
| 2,507,214 | 5/1950 | Medley | 604/84 |
| 2,849,256 | 8/1958 | Kowal | 604/85 X |
| 3,872,879 | 3/1975 | Green | 137/268 |
| 4,294,280 | 10/1981 | Tom | 137/268 |

Primary Examiner—Stephen C. Pellegrino
Attorney, Agent, or Firm—Paul L. Sabatine; Edward L. Mandell; Steven F. Stone

[57] ABSTRACT

A formulation dispenser is disclosed for use in a parenteral delivery system. The dispenser comprises an inlet for admitting fluid into the dispenser and an outlet for letting fluid leave the dispenser. A beneficial agent is housed in a formulation chamber in the dispenser and a membrane permeable to fluid and agent defines one boundary of the formulation chamber. A piston is slideably disposed in the dispenser for governing the flow of fluid through the dispenser, or for permitting fluid to contact the membrane and enter the formulation chamber for forming a solution containing agent that flows through the outlet into the parenteral system.

1 Claim, 9 Drawing Figures

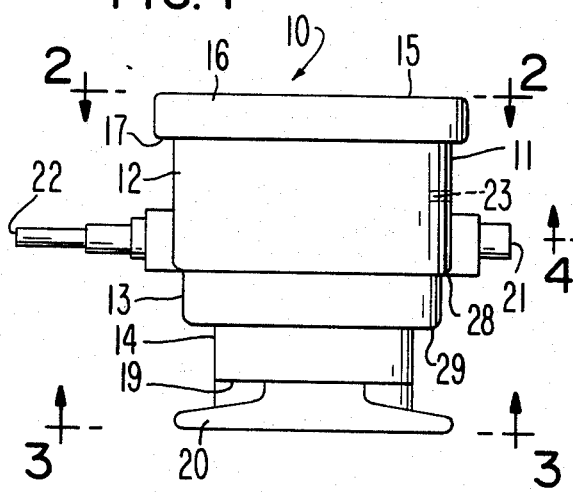
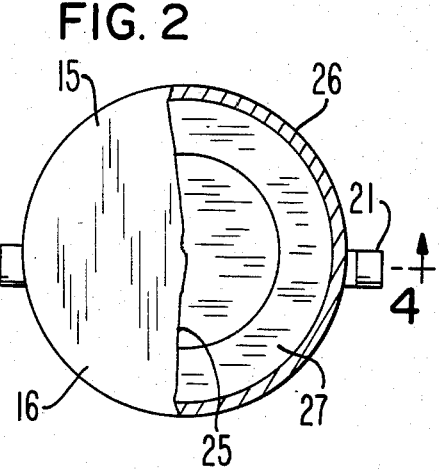
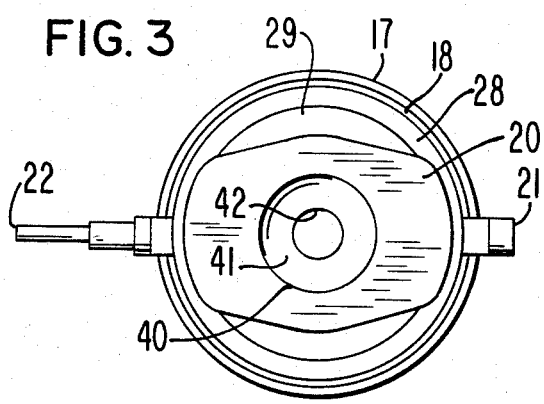
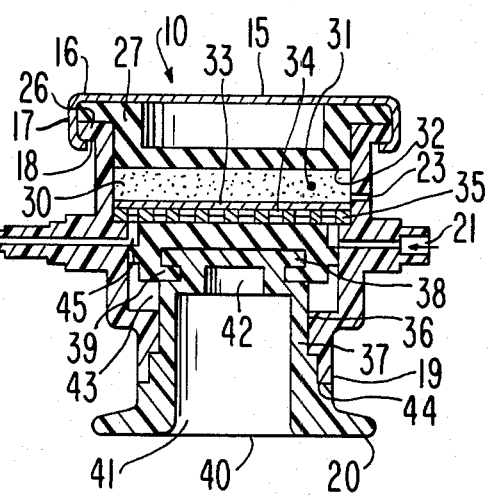
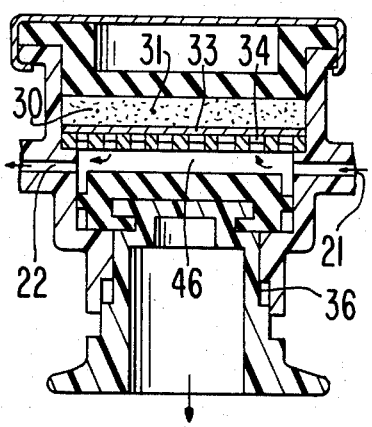
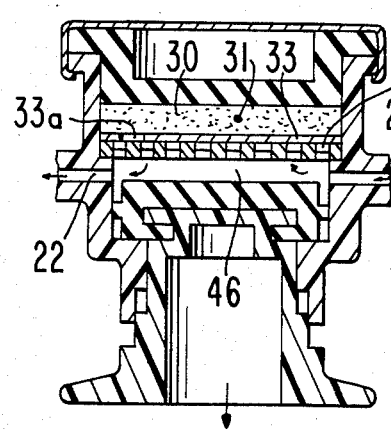
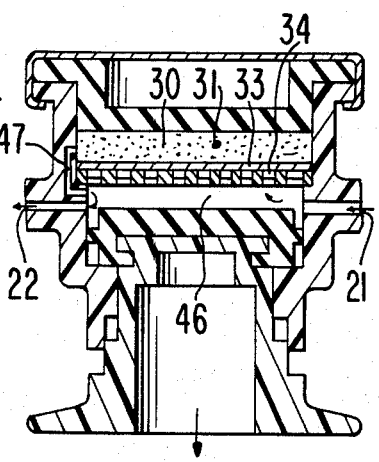

IN-LINE DRUG DISPENSER FOR USE IN INTRAVENOUS THERAPY

CROSS REFERENCE TO RELATED APPLICATIONS

This application is a continuation of U.S. patent application Ser. No. 06/518,490 filed July 29, 1983, U.S. Pat. No. 4,474,574 which application Ser. No. 05/518,490 is a continuation of U.S. patent application Ser. No. 06/338,206, filed Jan. 11, 1982, and now abandoned. These applications are assigned to the Alza Corporation of Palo Alto, Calif., which applications are incorporated herein by reference and benefit is claimed of their filing dates.

FIELD OF THE INVENTION

This invention pertains to a formulation dispenser comprising an agent formulation chamber and a piston chamber, which dispenser is adapted for use with a parenteral delivery system. The invention relates also to both a parenteral delivery system comprising the formulation dispenser, and to a method of parenterally administering an agent formulation using the parenteral delivery system comprising the formulation chamber.

BACKGROUND OF THE INVENTION

The parenteral administration of sterile fluids is an established clinical practice. The fluids are administered usually intravenously, and the practice is used extensively as an integral part of the daily treatment of medical and surgical patients. The fluids administered parenterally, usually intravenously, include aqueous solutions of dextrose, sodium chloride and various other electrolytes. The fluids commonly administered intravenously include blood and blood substitutes. Generally, the fluids are administered from a container that is suspended above a patient, with the fluid flowing from the container through an administration set connected to a hypodermic needle placed in a blood vessel, usually a vein of a patient. For intraperitoneal administration of fluids, the administration set is connected to a cannula traversing the abdominal wall of the patient.

The administration of fluids is a valuable and important component of patient care; moreover, the use of fluids has in recent years expanded beyond its original role of fluid and electrolyte replacement to include serving as the vehicle for the administration of beneficial agents, notably those which are desirable to administer by infusion via the intravenous, intraarterial, intraperitoneal or subcutaneous routes. For example, presently a beneficial agent, such as a drug, is administered intravenously by one of the following procedures: temporarily halting the flow of medical fluid, and intravenously administering the drug to the patient through an injection port in the administration set, followed by resumption of medical fluid into the patient; a drug is added to the fluid in the container, or into a volume control chamber in series with the administration set, and then carried by the flow of fluid to the patient; a drug is introduced into a so-called "piggyback" container, which is subsequently connected via a connector, in tributary fashion, to the primary administration set through which the medical fluid is administered to the patient; or a drug is administered by a pump which, by one of various recognized mechanical pumping actions, establishes flow and this determines the flow of fluid containing the drug into a flow path entering the patient, for example, an indwelling venous catheter.

While these delivery techniques are being used, they have certain disadvantages. For example, the administration of a drug through repeated injections into the administration set is inconvenient and represents each time a potential break in sterility; the use of pumps is expensive and sometimes inconvenient because of their size and weight; the rate of drug delivery to the patient is directly dependent on the flow of fluid with all currently practiced means of drug infusion; because of the relative chemical instability of aqueous solutions of many commonly used parenteral drugs, these procedures often require solubilization of the drug medication by the hospital pharmacist or nurse at a time proximate to its administration; and, while it is current practice to give some drugs by brief infusions, typically of 30 to 120 minutes duration repeated 3 or 4 times a day, they do not provide a means for (a) careful coordination of the procedures for solubilization and administration, and (b) careful regulation of the flow of drug solution during each period of infusion to insure that infusion is completed within the recommended time.

In view of this presentation, it is immediately apparent a critical need exists for a dependable and practical formulation dispenser for introducing a beneficial agent into a parenteral delivery system that overcomes the disadvantages associated with the prior art. It is also apparent that a pressing need exists for a formulation dispenser that can be used with a parenteral delivery system for clinically administering parenterally a beneficial agent at a controlled rate and in a beneficially effective amount to a patient according to a preselected program comprising continuous administration, repeated administration, at specified intervals of administration, or as needed administration.

DISCLOSURE OF THE INVENTION

Accordingly, a principle object of this invention is to provide both a novel and useful agent formulation dispenser adapted and designed for use with a parenteral delivery system for administering a fluid and a beneficial agent at a controlled rate according to a chosen regimen of administration and in an improved manner for optimizing the care of a warm-blooded animal whose prognosis benefits from parenteral administration.

Another object of the invention is to provide an agent formulation dispenser for admitting a beneficial agent into a parenteral fluid for optimizing the rate and the duration parameters of parenteral administration.

Another object of the invention is to provide an agent formulation dispenser comprising an agent chamber and a piston chamber for delivering an agent at a governed rate at preselected times into a medical fluid that flows through the dispenser.

Another object of this invention is to provide a formulation dispenser comprising (1) an agent chamber and (2) a piston chamber, and which dispenser can be used for improved health care by making available to the practitioner (a) a mechanism for administering a fluid, or (b) a mechanism for administering a fluid containing a beneficial agent by adjusting the position of the piston in the dispenser and thereby selecting concomitantly the (c) flow of fluid, or (d) the flow of fluid containing agent, for in either selection of their subsequent administration.

Another object of this invention is to provide a formulation dispenser that comprises a means for constituting an agent formulation in situ by dissolving a given amount of agent in a given volume of fluid present in the dispenser for its administration to a patient.

Another object of this invention is to provide a parenteral delivery system comprising a formulation dispenser for administering a known amount of a beneficial agent in a known volume of parenteral fluid.

Another object of the invention is to provide a parenteral delivery system comprising a formulation dispenser that makes available a regimen of agent administration comprising intervals of agent administration at a specified rate and for a specified duration, alternating with intervals during which no agent is delivered by the system.

Another object of this invention is to provide a parenteral delivery system comprising a formulation dispenser that makes possible converting a continuously functioning process of medical fluid administration into a process of agent formulation and administration that occurs at selected, predetermined periods of administration.

These objects, as well as other objects, features and advantages of this invention will become more readily apparent from the following detailed description, and the accompanying claims.

BRIEF DESCRIPTION OF THE DRAWINGS

In the drawings, which are not drawn to scale but are set forth to illustrate various embodiments of the invention, the Figures are as follows:

FIG. 1 is a perspective view of a formulation dispenser provided by the invention;

FIG. 2 is a view of the formulation dispenser seen at its formulation chamber end and partially opened for showing the closure components of the dispenser;

FIG. 3 is a view of the formulation dispenser at the piston chamber end thereof;

FIG. 4 is an opened, sectional view of the formulation dispenser along 4—4 of FIG. 2 depicting the internal structure of the dispenser and the piston in fluid flow position;

FIG. 5 is a sectional view of the formulation dispenser similar to the view of FIG. 4 depicting the internal structure and the piston in agent formulation position;

FIG. 6 is a view of the area enclosed in the circle of FIG. 5, depicting a flow path in the membrane that lets an agent solution leave the formulation chamber;

FIG. 7 illustrates another flow path that lets an agent solution leave the formulation chamber;

In the specification and the drawings, like parts in related Figures are identified by like numbers. The terms appearing earlier in the specification and in the description of the drawings are described hereafter in the disclosure.

MODES FOR CARRYING OUT THE INVENTION

Figure 8:
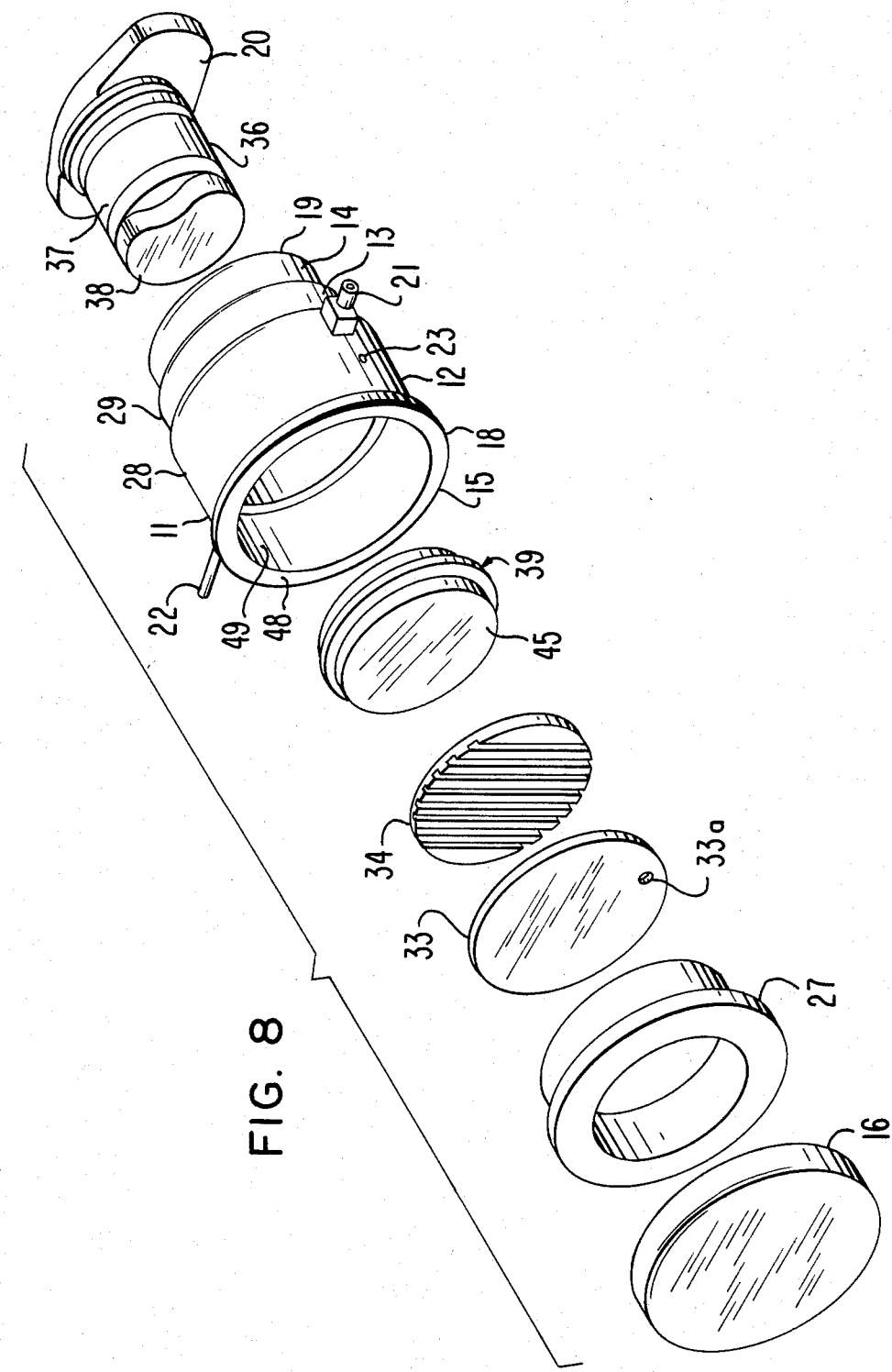
FIG. 8 is an exploded perspective view showing the members of the formulation dispenser; and, FIG. 9 is a view illustrating a parenteral delivery system comprising the formulation dispenser.

FIG. 1 represents a formulation dispenser provided by the invention and designated by the numeral 10. Formulation dispenser 10 is adapted for use in conjunction with a parenteral delivery system, such as an intravenous delivery system for administering to a recipient a medical fluid, or a medical fluid containing a beneficial agent added thereto in formulation dispenser 10. Formulation dispenser 10 comprises a housing 11 consisting of a first section 12, a second or middle section 13 of a slightly smaller cross-section and a third section 14 of slightly smaller cross-section. Housing 11 surrounds an internal lumen or space, and it is made from a metal or plastic, and in a preferred embodiment it is made from a transparent material such as a polycarbonate or the like. Dispenser 10 at one end 15 is closed by a retention cap 16, such as an aluminum cap that is crimped 17 about a flange 18 of housing 11. The opposite end 19 of dispenser 10 depicts a piston handle 20 protruding from housing 11. An inlet 21 is provided for admitting a medical fluid into dispenser 10 and an outlet 22 is provided for letting the medical fluid, or the medical fluid containing a beneficial agent leave dispenser 10. Inlet 21 and outlet 22 are adapted for placing dispenser 10 in a parenteral delivery system. An air vent 23 optionally present in housing 11 communicates with the interior of dispenser 10 and the exterior of the dispenser for letting air leave dispenser 10, while simultaneously preventing the flow of fluid therethrough.

FIG. 2 is a view of end 15 of formulation dispenser 10 as seen from 2—2 of FIG. 1. In FIG. 2, end 15 represents the entrance to dispenser 10. End 15 is used placing a dosage unit amount of beneficial agent in dispenser 10 and for placing the principal components of dispenser 10 therein during its assembly. End 15 is seen partially opened at 24 and it comprises wall 26 that forms hollow housing 11 and as noted is preferrably made of a transparent rigid plastic that is impermeable to fluid. A closure 27, such as a rubber stopper, is disposed snugly within end 15 for closing the end of dispenser 10. Retention cap 16 secures closure 27 in dispenser 10, and it also serves as a protective cap that maintains the sterility of the internal environment of dispenser 10.

FIG. 3 is a view of the opposite end 19 of dispenser 10 as seen from 3—3 of FIG. 1. In FIG. 3, end 19 represents the end of the dispenser containing a piston. The piston, as described in a later Figure, is used for letting a medical fluid pass through dispenser 10, or it is used for letting a medical fluid into dispenser 10 for mixing with a beneficial agent for forming in situ an agent solution, which in either instance leaves dispenser 10 for its eventual administration to a patient. End 19, as seen in FIG. 3, comprises crimped 17 outer rim of retention cap 16 that is crimped against the outwardly extending flange 18 formed integrally of the wall of the housing for effecting a sealing engagement between the retention cap, its crimped rim, and the flange. FIG. 3 also illustrates reduction 28 in the housing formed by smaller cross-section 17, reduction 29 formed by smaller cross-section 14, piston handle 20, inlet 21 and outlet 22. Elements 40, 41 and 42 are described in FIG. 4, and they represent a bore 40, that is extended as a longitudinal bore 41 and end in bore 42 in a piston, also seen in detail in FIG. 4.

In FIG. 4, dispenser 10 is seen in more detail, in opened section through 2—2 of FIG. 2. In FIG. 4, dispenser 10 comprises retention caps 16, its crimped rim 17, that is crimped against flange 18 formed from wall 26 and closure 27. Retention cap 16 and closure 27 close end 15, which end represents the entrance to formulation chamber 30 containing a beneficial agent 31. Formulation chamber 30 is the space for containing a dosage amount of beneficial agent 31 and it has as one boundary the surface 32 of closure 27 and it has as its inner boundary a release rate controlling membrane 33. Membrane 33 is supported by and it has one surface in contact with a membrane support 34. In an embodiment of the invention, membrane support 34 can be omitted when membrane 33 is thick enough to be self-supported in the dispenser. Membrane support 34 has its outer edge abutting against an inner shoulder 35 formed by the inwardly reduction in the cross-section of wall 26. Membrane support 34 is designed like a grid with holes or channels, or like a screen and it is made of metal or of plastic and it is freely permeable to the passage of fluid. Release rate controlling membrane 33 is permeable to the passage of fluid, and it can be formed of a microporous, diffusional, or an osmotic type polymer, that maintains its physical and chemical integrity during the agent delivery period of dispenser 10. The beneficial agent is in contact with the outer surface of membrane 33 and closure 27 that forms the outer faced boundary of formulation chamber 30. A vent 23 is optionally provided with dispenser 10 for evacuating trapped air for dispenser 10, and it is optionally made of a material that prevents the entrance of bacteria into dispenser 10.

On the opposite faced surface of membrane support 34, a piston 36 is slidably disposed in the lumen of dispenser 10. Piston 36 is in the lumen defined by the reduced inner cross-section of housing 11 and it is generally termed piston chamber 43. Piston 36 comprises piston handle 20 that protrudes through an opening 44 in end 19 of housing 11, integrally formed with piston shaft 37 that terminates in piston end 38. A piston head 39 fits tightly over piston end 38 and it is made of rubber or the like. An opening 40 in piston handle 20 extends as a longitudinal bore 41 the length of piston shaft 37 and it leads to an inner bore 42 having a reduced circumference in piston end 38. The surface of piston head 39 facing formulation chamber 30 has at the periphery of the faced surface, a slightly smaller circumference around this outer perimeter forming a fluid flow path 45 around the perimeter on the piston head. Flow path 45, when the piston is disposed fully in the dispenser, aligns with inlet 21 and outlet 22 for permitting an incoming medical fluid to flow through dispenser 10. Piston head 39 seats snugly against support 34 when the piston is pushed or placed against support 34; and, in this position an incoming fluid does not enter formulation chamber 30, rather it flows in the path around the perimeter and through the dispenser as indicated by the flow arrows in FIG. 4.

FIG. 5 depicts formulation dispenser 10 adding beneficial agent 31 to an incoming medical fluid, thereby forming in situ a medical solution containing the beneficial agent. In FIG. 5, when piston 36 is pulled outward, as indicated by the direction arrow at piston handle 20, piston head 39 moves away from membrane support 34, for establishing a passageway 46, perpendicular to and between membrane support 34 and piston head, through dispenser 10. Passageway 46 establishes a fluid communication means with formulation chamber 30. In this operative position, incoming fluid entering through inlet 21 passes through membrane support 34, rate controlling membrane 33, into formulation chamber 30, wherein it mixes with beneficial agent 31 and forms an agent solution that passes from formulation chamber 30, reenters passageway 46 and leaves dispenser 10 through outlet 22.

FIG. 6 depicts another embodiment whereby an agent solution can leave formulation chamber 30. In FIG. 6 membrane 33 is manufactured with a hole 33a, and as agent solution is formed in formulation chamber 30, it flows through hole 33a, through membrane support 34 made as a screen or from a porous material, and into passageway 46 for its subsequent flow from dispenser 10.

FIG. 7 illustrates yet another embodiment for letting an agent solution leave formulation chamber 46. In this embodiment, an agent formulation solution leaves formulation chamber 30 through a channel 47. Channel 47 in housing wall 26 permits flow around membrane 33, membrane support 34, into passageway 46 for flow through exit port 22.

The agent in the chamber can be in any pharmaceutical state that forms an agent formulation with a medical fluid that enters the chamber, and the use of the chamber with an agent therein does not require any reconstitution, or admixture prior to use. Exemplary pharmaceutically acceptable forms that can be used in the chamber include solid, crystalline, microcrystalline, particle, pellet, granule, powder, tablet, spray-dried, lypohilized, forms that dissolve or undergo disintegration and dissolution in the presence of a parenteral fluid including intravenous fluids, and/or the like. The agent formulation chamber generally will store an amount of agent for executing a prescribed therapeutic or beneficial program. That is, an amount of agent for the preprogrammed, delivery of a therapeutically or a beneficially effective amount of the agent to produce a therapeutic or a beneficial result. The agent formulation chamber generally will have a capacity of from about 10 milliliters to 200 milliliters of fluid or more, and it can house from about 5 milligrams to 20 grams of agent or more. The expression beneficial agent, as used herein, generically denotes any substance that produces a therapeutic or a beneficial result, such as a drug, a carbohydrate, an electrolyte and/or the like. The term fluid or liquid denotes a fluid, or a liquid that can be administered parenterally including intravenously, comprising pharmaceutically acceptable fluids that are also a pharmaceutically acceptable carrier for an agent, such as water, isotonic saline, Ringer's lactate, and the like. The term formulation, and agent formulation as presently used herein, generically indicates the beneficial agent is formulated, mixed, added, dissolved, suspended, solubilized, and formulated into a solution, carried and/or the like in or by the fluid in a physical-chemical form acceptable for parenteral including intravenous administration. The flow of medical fluid into the formulation chamber can be started, stopped or regulated by the piston that permits an incoming fluid to pass through the dispenser or to pass into the formulation chamber, and correspondingly the flow of agent solution from the dispenser.

FIG. 8 is an exploded perspective view showing the members comprising formulation dispenser 10. The members are housing 11 consisting of first section 12, second section 13 and third section 14. Housing 11 at its end 15 has a flanged 18 opening 48 that leads to internal space 49, and at its opposite end 19, it has an opening, not seen in FIG. 8, for accommodating piston 36. Housing 11 has an inlet 21, and outlet 22 and an air vent 23. Piston 36 comprises piston shaft 37 terminating in piston handle 20 and piston receiving end 38. Piston head 39 fits onto end 38 and it is formed with flow path 45 for permitting a fluid to flow around head 39 and through the dispenser. FIG. 8 also depicts membrane support 34, membrane 33 optionally formed with aperture 33a, closure 27 and retention cap 16.

Figure 9:
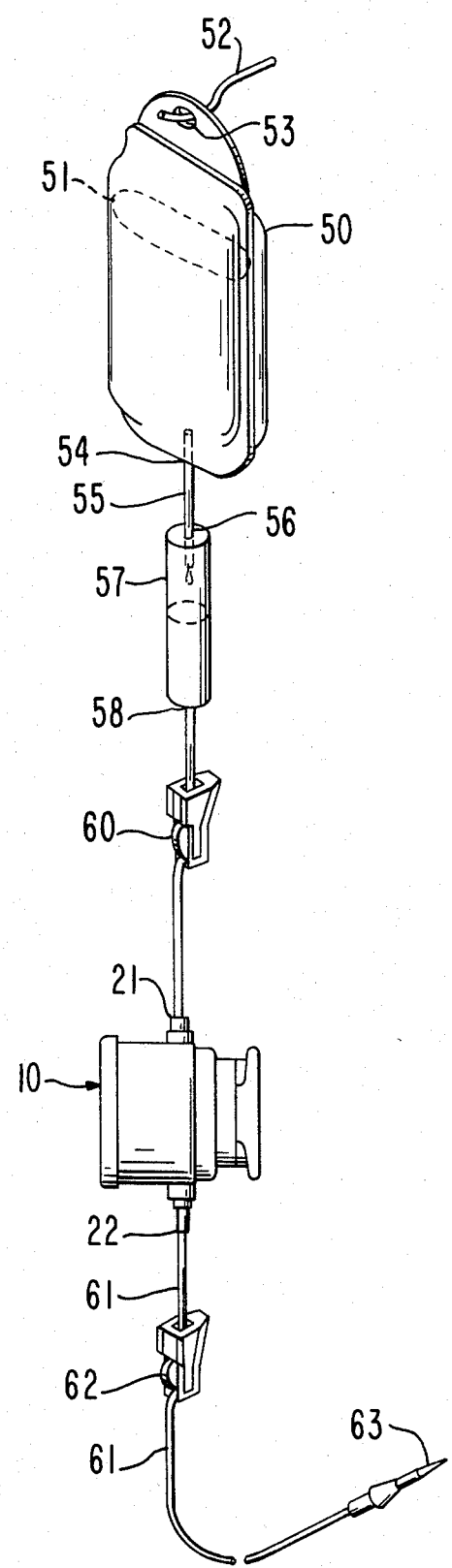

FIG. 9 illustrates a parenteral delivery system comprising dispenser 10. The parenteral delivery system comprises a container 50 formed of a flexible or a semi-rigid, preferably transparent plastic, such as a polyolefin or a polyvinyl-chloride, and it contains a medical fluid 51 adapted parenteral including intravenous administration. Medical fluid 51 also is a pharmaceutical vehicle or carrier for a beneficial agent that is to be administered to a recipient. Container 50, in the embodiment illustrated, is non-vented, the medical fluid in it is at atmospheric pressure, and the container collapses as it empties of fluid 51. Container 51 is adapted to be hung neck-down from a hanger 52 by a hole 53 in a bib formed integral with container 50. The parenteral delivery system can use other containers such as a vented-type container that requires air to operate. Air enters this type of container through an air filter usually formed as part of a drip chamber, or air can enter this type of container through an internal venting tube that allows air to enter the container as fluid is infused into a patient. Container 50, at its neck end distant from its hanging end, has an administration port 54 adapted for receiving an administration set.

The administration set provided by this invention is used to deliver medical fluid 51 and a beneficial agent to a patient. The administration set is sterile, pyrogen-free and disposable. The set comprises the components described hereafter, and it connects with port 54 of container 11 via hollow connector 55. Connector 55 is adapted to receive end 56 of drip chamber 57, which is used to trap air and permit adjustment of the flow rate of fluid 51 from container 50 as the flow proceeds dropwise. An outlet 58 of drip chamber 57 connects to tube 59 that goes through an optional roller clamp 60. Roller clamp 60 can be used for pinching the internal diameter of tube 59 to regulate flow therethrough. As tube 59 passes through clamp 60 it connects to inlet 21 of dispenser 10, described above, which dispenser is used for introducing a beneficial agent into a medical fluid. A second segment of tube 61 connects to outlet 24 of the dispenser, passes through primary roller clamp 62 that is used in cooperation with sight drip chamber 57 for adjusting the fluid flow rate from dispenser 10 and to an adapter-needle assembly 63 for conveying medical fluid and agent into a vein and sometimes an artery of a patient.

The parenteral delivery system comprising the agent dispenser can be used for the administration of many beneficial agents especially where it is desirable to administer by infusion, and more particularly via the intravenous, intra-arterial, intraperitoneal or subcutaneous routes. For example, the delivery system can be used in one presently preferred embodiment, in intravenous fluid replacement, such as administering plasma or saline and simultaneously or intermittently administering a therapeutically effective amount of drug therewith; in another embodiment as a method in intravenous electrolyte-balance replacement, such as supplying sodium, potassium or chloride ions with drug administered therewith to a patient in need of electrolyte restoration and an intravenous drug; and in a method of intravenous nutrition, such as supplying dextrose and concomitantly administering or periodically administering a parenterally administrable drug to a patient in need of such therapies.

The novel and useful invention provides a system and method for obtaining the precise control of agent administration to a recipient. While there has been described and pointed out features of the invention as applied to presently preferred embodiments, those skilled in the art will appreciate that various modifications, changes, additions and omissions in the invention illustrated and described can be made without departing from the spirit of the invention.

I claim:

1. An intravenous system for delivering a drug formulation, wherein the intravenous system comprises:
   (a) a reservoir of an intravenously acceptable fluid;
   (b) a formulation dispenser in fluid communication with the reservoir, the formulation dispenser comprising:
   (1) a housing surrounding an internal lumen, the housing having openings at its opposite ends;
   (2) piston means disposed in one opening of the housing;
   (3) a beneficial drug in the housing present in an effective amount for producing a therapeutic effect, said drug a member selected from the group consisting of solid, crystalline, granule, power, tablet, dried and lyophilized pharmaceutically acceptable forms that produce an intravenously administrable drug formulation when contacted by fluid that enters the dispenser;
   (4) a fluid permeable membrane in the housing positioned between the drug and the piston;
   (5) a closure disposed at the other opening of the housing facing the drug;
   (6) inlet means in the housing for letting fluid enter the housing and contact the beneficial drug; and,
   (7) outlet means in the housing for letting intravenously administrable drug formulation leave the housing.

* * * * *